United States Patent [19]

Smith

[11] Patent Number: 5,537,164

[45] Date of Patent: Jul. 16, 1996

[54] RETROILLUMINATING INDIRECT GONIOPRISM

[76] Inventor: Alan D. Smith, 5757 Colorado Ave., Odessa, Tex. 79762

[21] Appl. No.: 359,701

[22] Filed: Dec. 20, 1994

[51] Int. Cl.$^6$ ................................... A61B 3/00
[52] U.S. Cl. .................... 351/219; 351/205; 351/246
[58] Field of Search ........................ 351/219, 214, 351/212, 211, 247, 246, 205; 606/4, 6, 107

[56] References Cited

U.S. PATENT DOCUMENTS

| | | | |
|---|---|---|---|
| 2,430,851 | 11/1947 | Allen | 351/205 |
| 3,001,441 | 9/1961 | Herbert . | |
| 3,409,349 | 11/1968 | Boyle et al. . | |
| 3,589,800 | 6/1971 | Cardona | 351/16 |
| 3,630,602 | 12/1971 | Herbert | 351/16 |
| 3,780,979 | 12/1973 | de Guillebon | 351/16 |
| 3,820,879 | 6/1974 | Frisen | 351/1 |
| 3,828,788 | 8/1974 | Krasnov et al. | 128/303.1 |
| 3,943,931 | 3/1976 | Krasnov | 128/303.1 |
| 3,944,341 | 3/1976 | Pomerantzeff | 351/7 |
| 3,954,329 | 5/1976 | Pomerantzeff | 351/16 |
| 4,033,679 | 7/1977 | Sussman | 351/16 |
| 4,056,310 | 11/1977 | Shimizu et al. | 351/6 |
| 4,134,647 | 1/1979 | Ramos-Caldera | 351/6 |
| 4,378,147 | 3/1983 | Fujita | 351/205 |
| 4,439,026 | 3/1984 | Wilms | 351/219 |
| 4,452,514 | 6/1984 | Spitznas | 351/206 |
| 4,502,764 | 5/1985 | Riquin | 351/160 R |
| 4,506,962 | 3/1985 | Roussel | 351/160 R |
| 4,553,824 | 11/1985 | Abe | 351/219 |
| 4,558,698 | 12/1985 | O'Dell | 128/203.1 |
| 4,568,984 | 7/1986 | Kurwa | 351/160 R |
| 4,598,984 | 7/1986 | Rol | 351/219 |
| 4,664,490 | 5/1987 | Rol | 351/219 |
| 4,753,526 | 6/1988 | Koester | 351/219 |
| 4,799,784 | 1/1989 | Safir | 351/212 |
| 4,838,266 | 6/1989 | Koziol et al. | 128/303.1 |
| 4,907,872 | 3/1990 | Schirmer et al. | 351/160 R |
| 4,964,717 | 10/1990 | Koester | 351/219 |
| 4,966,452 | 10/1990 | Shields et al. | 351/219 |
| 4,973,330 | 11/1990 | Azema et al. | 606/5 |
| 5,000,751 | 3/1991 | Schröder et al. | 606/4 |
| 5,024,518 | 6/1991 | Richards et al. | 351/219 |
| 5,032,020 | 7/1991 | Robert | 351/219 |

(List continued on next page.)

*Primary Examiner*—William L. Sikes
*Assistant Examiner*—Hung Xuan Dang
*Attorney, Agent, or Firm*—Akin, Gump, Strauss, Hauer & Feld

[57] ABSTRACT

A retroilluminating indirect gonioprism comprising an optical prism, an oblique reflector and light baffle to reduce the intensity of light reflected from the gonioprism anterior surface back toward an observer, and an opaque surface to substantially prevent retinal burns when using the gonioprism with a directed energy beam. Retroillumination of anterior chamber structures is provided by fiber optics incorporated into the gonioprism housing which direct light from an external source into the limbal region of the eye. This retroillumination increases the accuracy of identification of structural landmarks (e.g., the scleral spur) which are important in argon laser trabeculoplasty. A directed energy beam, as from a high energy laser, may be directed through the gonioprism while an eye structure on which the beam is focussed is observed through the gonioprism. First-surface reflection of a portion of the directed energy beam passes obliquely toward a light baffle and is substantially absorbed, while the transmitted portion of the beam is slightly laterally displaced and strikes the gonioprism anterior surface. The portion of the beam reflected from the gonioprism anterior surface back toward the observer again undergoes partial reflection oblique to the visual axis and slight lateral displacement before reaching the observer. Thus, the amount of light reflected from the gonioprism anterior surface back toward an observer is reduced. Substantial optical correction for astigmatism of oblique incidence and for assuring substantial parallelism between the observer's line-of-sight to the gonioprism and the gonioprism optical axis is preferably provided through appropriate configuration of at least one substantially convex surface which comprises at least a portion of the optical prism anterior surface.

24 Claims, 4 Drawing Sheets

U.S. PATENT DOCUMENTS

| | | | |
|---|---|---|---|
| 5,046,836 | 9/1991 | Volk | 351/219 |
| 5,094,523 | 3/1992 | Reznichenko et al. | 351/221 |
| 5,123,902 | 6/1992 | Müller et al. | 604/21 |
| 5,152,760 | 10/1992 | Latina | 606/6 |
| 5,163,934 | 11/1992 | Munnerlyn | 606/5 |
| 5,200,773 | 4/1993 | Volk | 351/219 |
| 5,216,456 | 6/1993 | Volk | 351/214 |
| 5,233,372 | 8/1993 | Matsumoto | 351/221 |
| 5,252,998 | 10/1993 | Reis et al. | 351/160 R |
| 5,255,025 | 10/1993 | Volk | 351/205 |
| 5,277,911 | 1/1994 | Viegas et al. | 424/427 |
| 5,309,187 | 5/1994 | Crossman et al. | 351/219 |
| 5,329,322 | 7/1994 | Yancey | 351/211 |
| 5,337,094 | 8/1994 | Mizuno et al. | 351/206 |
| 5,342,370 | 8/1994 | Simon et al. | 606/107 |
| 5,347,326 | 9/1994 | Volk | 351/160 R |
| 5,349,398 | 9/1994 | Koester | 351/212 |
| 5,349,399 | 9/1994 | Sekine | 351/215 |
| 5,359,372 | 10/1994 | Kida et al. | 351/219 |

RETROILLUMINATING INDIRECT GONIOPRISM

BACKGROUND

Field of the Invention

The present invention relates to methods and apparatus for examining and treating structures within the eye and in particular to indirect gonioprisms.

Gonioscopy and Angle Structures

"Gonio" is Greek for angle. Gonioscopy refers to an examination of the angle structures in the anterior chamber of the eye. The angle of the eye is formed by the insertion of the peripheral iris into the wall of the eye. The angle includes a portion of the anterior ciliary body, the base of the iris processes, the trabeculum (uveoscleral, corneoscleral and juxtacanalicular meshworks), the scleral spur, Schlemm's canal, Schwalbe's line and the adjacent cornea. Examination of these angle structures is currently performed by some variation of one of two techniques, i.e., direct or indirect gonioscopy.

Direct Gonioscopy

Direct examination of anterior chamber angle structures requires special lenses and techniques because light rays projecting from one or more angle structures may be strongly refracted as they leave the eye. Such rays first pass through the aqueous humor which fills the anterior chamber and then enter the cornea, passing through the corneal endothelium and corneal stroma, and finally exit the eye by passing through the corneal epithelium and entering the tear film which covers the cornea. The light rays exit the tear film and then enter a medium (air) having a relatively lower index of refraction than the tear film at an angle of incidence greater than the critical angle for total internal reflection (TIR). This means that the light rays are bent back tangentially toward the corneal epithelium and thus do not escape the tear film, so they cannot form an image outside of the eye.

To circumvent TIR of light rays emanating from angle structures and thereby allow direct gonioscopy, a contact lens is placed on the cornea in conjunction with a coupling medium (e.g., a physiological salt solution between the lens and the cornea) to shift the air interface to the anterior surface of the contact lens. Light rays projecting from angle structures can then pass through the corneal epithelium and coupling fluid and proceed into the contact lens without encountering a medium having a relatively lower index of refraction than the medium they are leaving. Along this path a portion of the light rays may be reflected at each interface, but TIR would not occur unless it was at the air interface with the anterior lens surface (and it may be avoided there too). To ensure that TIR does not occur and to facilitate direct gonioscopy, the anterior (air interface) surface of the contact lens is made with a very short radius of curvature. This strongly curved lens allows object rays from angle structures to enter the air which lies beyond the anterior contact lens-air interface at an angle of incidence less than the critical angle for TIR.

Having provided for escape of the imaging light rays from the contact lens, the direct gonioscopy technique also employs a hand-held light source to illuminate the angle structures and a hand-held or counterbalance dampened gonioscope to visualize the angle structures through the contact lens. The gonioscope allows a binocular view of the angle with magnification in the range of 16× or greater. The advantages of this examination technique include easy orientation to eye landmarks for the examiner and easy comparison of various angle structures by quick movements of the examiner's glance. Additionally, simultaneous examination of both eyes for comparison of angle structures is possible with bilaterally applied lenses, and the examiner can maneuver the light source to highlight angle structures and avoid or reduce unwanted corneal reflections, especially in clouded corneas.

Indirect Gonioscopy

As in direct gonioscopy, the indirect technique employs a corneal contact lens, but the indirect lens contains one or more mirrored surfaces which redirect the light rays emanating from an angle structure toward an exiting surface of the lens. The internal reflective surface(s) facilitate the rays' approach to the lens-air interface at the exiting surface at less than the critical angle for TIR. Indirect gonioscopy employs the use of a slit lamp biomicroscope to provide light and stereoscopic visualization of images produced by the goniolens. Thus, the patient can be more conveniently positioned in a sitting position, whereas for direct gonioscopy the patient is commonly in a reclining or supine position. The sitting position is preferable for treatment procedures involving the direction of laser light into the eye.

During indirect gonioscopy, examination of different angle structures is facilitated by rotating the mirror plane or by tilting the lens to change the mirror angle. The technique is termed indirect because the structure images are reflected from the mirror surface and are inverted. The main disadvantages of the technique are the inability to simultaneously image the angles of both eyes and the limitations imposed by the slit lamp in positioning of the light.

Gonioscopy Lenses in Surgery

In addition to their use in diagnostic examination of angle structures, both direct and indirect gonioscopy have also been adapted to surgical and laser therapy of the eye. Direct gonioscopy lenses, for example, are used in a surgical procedure for congenital glaucoma known as goniotomy. Indirect gonioscopy lenses, on the other hand, are used in argon laser trabeculoplasty, goniophoto-coagulation and goniopuncture techniques. The efficacy of each of these procedures is directly linked to visualizing angle structures to determine the presence of pathology, the need for treatment, and the effects of directed energy beams on eye structures. Devices and techniques which would enhance visualization and identification of angle structure landmarks could potentially improve efficacy and reduce morbidity in treated patients. Better visualization would also allow more accurate identification of normal variations (as distinguished from pathologic states) in angle structures, thus avoiding unnecessary surgery.

Besides the need for better visualization with indirect gonioscopy, additional eye protection is desirable for surgeons who direct relatively high-energy beams through a gonioprism as part of certain therapies. At least a portion of a light energy beam which is directed toward an eye structure via a gonioprism will not reach the structure because it will be reflected instead from the anterior surface of the gonioprism. Since the beam is commonly directed to the gonioprism along a portion of the visual path from the surgeon observer to the gonioprism, at least a portion of the light reflected from the gonioprism anterior surface tends to return directly to the eye of the observer. Significant long-term eye damage resulting from such reflected energy has been reported in surgeons. Use of a gonioprism having an oblique anterior surface has been proposed to redirect away from the observer any light that is not transmitted, but light rays exiting this inclined anterior surface to form an image are also redirected in the same direction. To maintain optimal visualization, a surgeon must tilt the prism in the direction opposite the inclination or peer at an angle more normal to the anterior surface of the prism. Thus, either action tends to negate the beneficial effects of the oblique surface in redirecting reflected light.

Another safety issue in existing gonioprisms concerns the possibility of accidental retinal damage occurring in patients undergoing gonioscopy when a high-intensity light beam is inadvertently directed through a gonioprism without striking a reflecting surface to direct it to angle structures. Such a beam can and occasionally does proceed directly to the retina where a burn may be produced.

SUMMARY OF THE INVENTION

The present invention comprises a retroilluminating gonioprism which enhances visualization of anterior chamber structures and provides improved safety features for surgeons using the device and for patients. The gonioprism comprises a substantially frusto-pyramidal optical prism having a longitudinal axis (i.e., substantially the prism optical axis) and comprising a prism base, at least three (preferably eight) substantially similarly shaped (preferably substantially planar) prism sides, and a substantially concave posterior surface opposite the prism base. The prism base, in turn, is an anterior surface and the anterior surface comprises at least one substantially convex (preferably substantially spherical) surface. Each prism side is preferably oriented at an angle of about 25 to about 30 degrees with respect to the optical prism longitudinal axis.

At least a portion of light entering the prism through the posterior surface (which in use rests on the cornea) is at least partially reflected from at least one prism side and exits the prism through at least one substantially convex surface substantially focussed external to said prism. Optical correction to reduce astigmatism of oblique incidence and to bring the observer's line of sight closer to substantial parallelism with the optical axis of the retroilluminating gonioprism is preferably applied at the (at least one) substantially convex anterior surface. This choice of correction site tends to simplify fabrication and/or minimize the required size of the light baffle (see below). However, correction may also be applied by altering the prism sides to make them, for example, substantially spherical, substantially cylindrical, substantially conical or substantially toroidal. Where correction desired at the (at least one) substantially convex surface differs from that obtainable with spherical curve(s), the convex surface(s) may comprise substantially cylindrical or substantially toroidal portions. Complementary alterations of both prism sides and the prism anterior surface(s) are in general combined to attain both line-of-sight and astigmatic corrections, but in the preferred embodiment schematically illustrated in the accompanying figures, internally reflecting portions of the prism sides are substantially plane, while the astigmatic and line-of-sight corrections are incorporated in the above convex surface(s).

A gonioprism of the present invention also comprises a plurality of fiber optics coupled to the prism posterior surface to project light beyond that surface into the eye tissues on which the surface rests while in use. The fiber optics are preferably arranged substantially symmetrically around the posterior surface and are preferably directed to project light substantially parallel to the prism longitudinal axis to produce scleral scatter lighting in a cornea under the posterior surface and retroillumination of certain anterior chamber structures.

A reflector is positioned proximate the prism base and coupled to the prism to substantially prevent either translation or rotation of the prism with respect to the reflector. The reflector comprises at least one plano-flat lens oriented obliquely with respect to the prism longitudinal axis to reflect at an angle oblique to the longitudinal axis at least a portion of light traveling substantially parallel to the longitudinal axis and striking the reflector. Transmission of light (e.g., a directed energy beam from a laser) directly through the optical prism to the retina of a patient without deviation by a prism side reflecting surface is substantially prevented by an opaque surface making at least a portion of the reflector opaque, the opaque surface being substantially centered about the longitudinal axis and preferably substantially non-reflective.

A light baffle is positioned adjacent to the reflector and coupled to both the reflector and the optical prism. The light baffle is configured to absorb at least a portion of light which, after traveling substantially parallel to the prism longitudinal axis, strikes the reflector and is reflected obliquely with respect to the longitudinal axis from the reflector toward the light baffle. A light baffle may preferably take the form of a hollow and open-ended substantially right circular cylinder having a longitudinal axis substantially collinear with the prism longitudinal axis. A configuration to absorb at least a portion of light falling on the inner surface of such a light baffle may alternatively comprise an inner surface coating which approximates a blackbody surface, or a ridged inner surface which facilitates multiple reflection and absorption of light striking the surface obliquely. The blackbody surface may be approximated by adhering, for example, lamp black to the surface. Such a surface may absorb at least 70 percent of light striking it. On the other hand, a ridged inner surface may be cast or cut from a solid form of glass, plastic or other substantially transparent material. If a ridged form is chosen and a substantially monochromatic light source is to be used with it (e.g., laser light), the peak-to-peak spacing and depth of the inner surface ridges may be such as to encourage destructive interference as light reflected from different ridges interacts. In addition to such destructive interference, about 4 percent light reflection is expected at each interface (i.e., each discontinuity in index of refraction).

Substantially surrounding the optical prism of the present invention is a substantially conical double-wall housing coupled to the prism. The double-wall housing comprises an inner wall to shield the prism sides from contact with stray light (e.g., room light), fluids or solid matter, and an outer wall which may be used for gripping and/or positioning the gonioprism. At least a portion of the fiber optics which are coupled to the posterior surface are substantially symmetrically arranged between the inner and outer walls, and the outer wall comprises a plurality of fenestrations for allowing light from (the distal end of each of) the fiber optics to be transmitted from the conical housing (preferably in a direction substantially parallel to the prism longitudinal axis).

Light for the fiber optics originates in a separate source and is transmitted to the double-wall housing through an elongated hollow handle firmly coupled to double-wall housing and comprising at least a (more proximal) portion of the fiber optics within the hollow handle. In preferred embodiments of the retroilluminating gonioprism, the above fiber optics may terminate near the end of the hollow handle which is not coupled to the double-wall housing. This termination may then comprise a fiber optic coupler and (preferably threaded or twist-lock) connector for coupling the gonioprism fiber optics to an external light source through an intermediate fiber optic. Such an arrangement would facilitate easy coupling and decoupling of (disposable) retroilluminating gonioprisms.

Note that in the gonioprism of the present invention each prism side may comprise an air interface at which at least a portion of light entering said prism through said posterior surface would be totally internally reflected. Alternatively, each prism side may comprise a substantially reflective metallic film. The choice of side configuration may depend on the choice of fabrication technique for the prism.

The optical prism may comprise optical glass or a substantially transparent plastic such as polymethyl methacrylate. In the latter case, the prism may be injection molded to reduce costs for a disposable embodiment of the gonioprism. Whether glass or plastic, portions of the gonioprism (including the reflector and the anterior surface) may be given an antireflective coating of, for example, magnesium fluoride in a one-quarter wavelength thickness.

The present invention also comprises a method of reducing reflection of light from a gonioprism anterior surface to an observer who is using the gonioprism to observe ocular structures, the gonioprism having an optical axis substantially collinear with its longitudinal axis. The method comprises inserting a plano-flat lens between the observer and the gonioprism anterior surface and positioning the flat lens oblique to a line-of-sight from the observer to the gonioprism anterior surface. One then provides a light baffle to absorb at least a portion of light reflected from the plano-flat lens, the light having traveled substantially along a line from the observer toward the gonioprism anterior surface. Finally, one configures the gonioprism anterior surface to substantially correct astigmatism of oblique incidence and to substantially restore parallelism between the line-of-sight and the gonioprism optical axis. As above, the method may additionally comprise adding an antireflective coating to either the gonioprism anterior surface or the plano-flat lens or both.

Note that in the above method as well as in the description of the retroilluminating gonioprism itself, each plano-flat lens is preferably positioned between about 60 degrees and about 80 degrees oblique to a line from the observer to the gonioprism anterior surface. This line will generally be substantially parallel to but not collinear with the prism longitudinal axis.

The gonioprism of the present invention thus allows enhanced visualization of angle structures through retroillumination of them. Although retroillumination is normally limited to the direct gonioscopy technique, the retroilluminating gonioprism incorporates a mirrored prism system and the indirect technique. Benefits of this system include: better visualization through clouded corneal media, improved distinction of iris processes from peripheral anterior synechiae, easier detection of small lens dislocations, enhanced view and identification of scleral spur and Schlemm's canal, improved ability to see Krukenberg's spindle and interstitial corneal vessels, and retroillumination of anterior ciliary body tumors and iris cysts. The use of eight mirrored surfaces allows better alignment of the mirror plane with its opposing angle segment. This reduces image blur associated with astigmatism of oblique incidence.

DETAILED DESCRIPTION

Figure 1A:
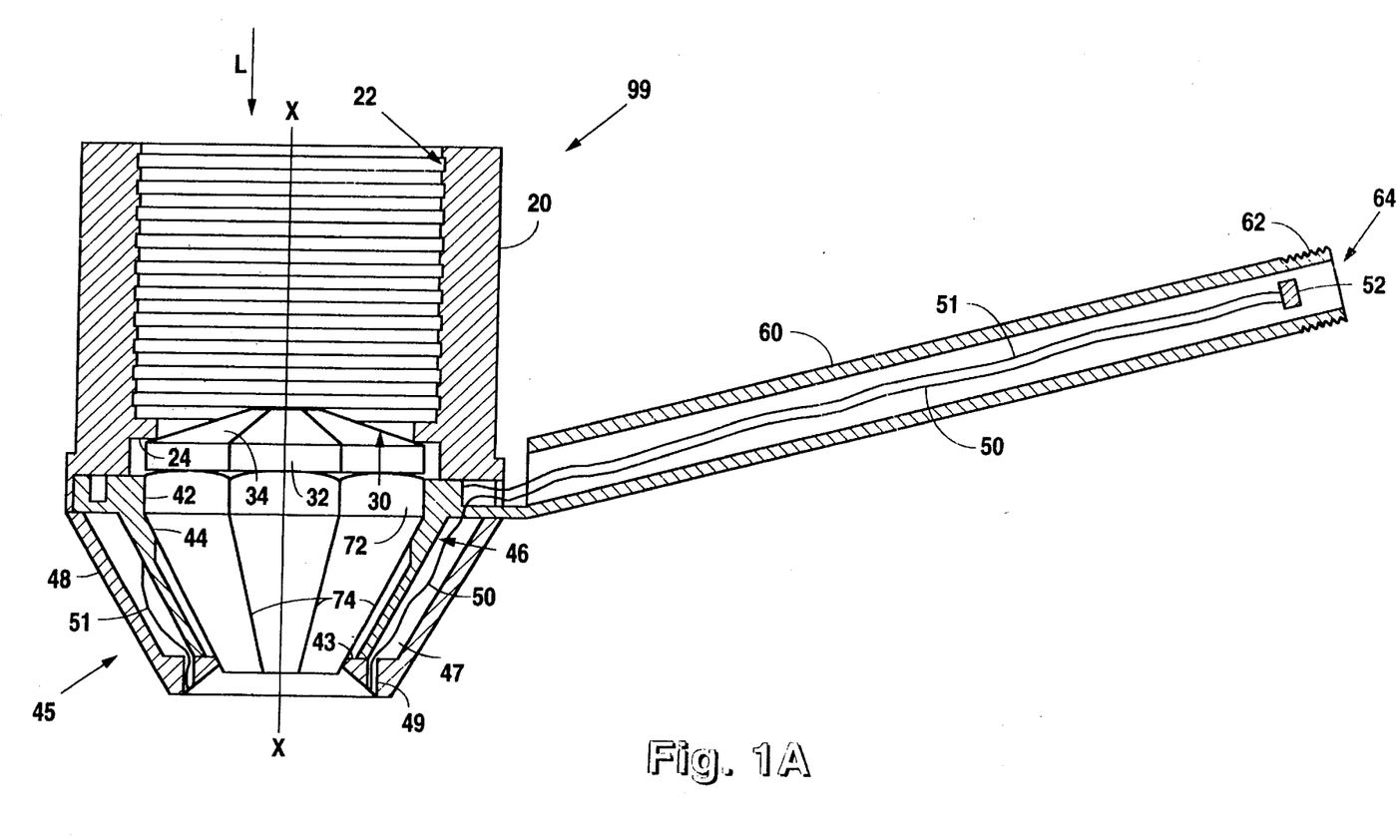
FIG. 1A schematically illustrates a cutaway view of the hollow handle, light baffle and double-wall housing, exposing fiber optics and a side elevation of the prism and reflector.
Figure 1B:
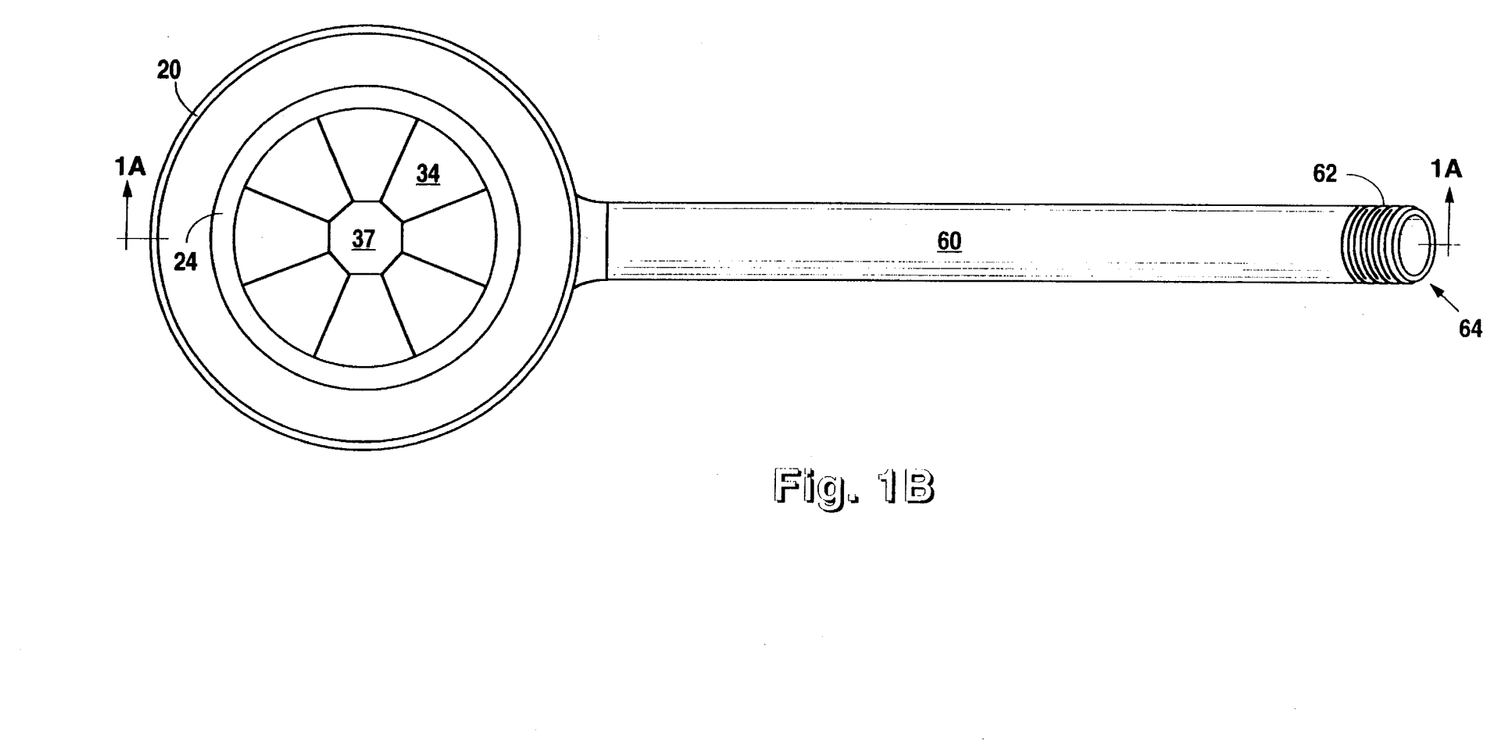
FIG. 1B schematically illustrates a top elevation of the retroilluminating gonioprism.
Figure 2A:
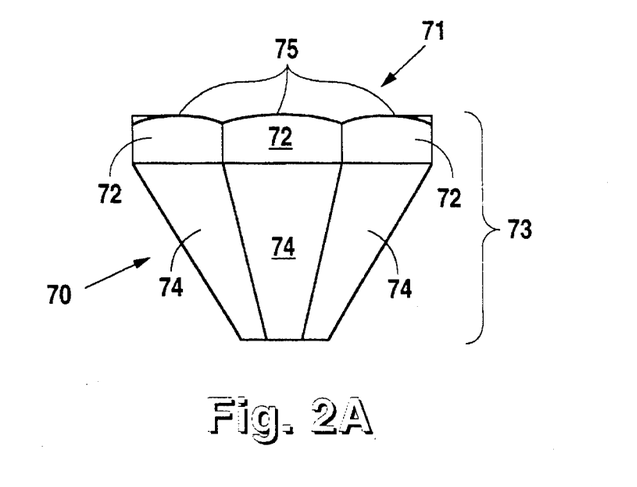
FIG. 2A schematically illustrates a side elevation of the prism.
Figure 2B:
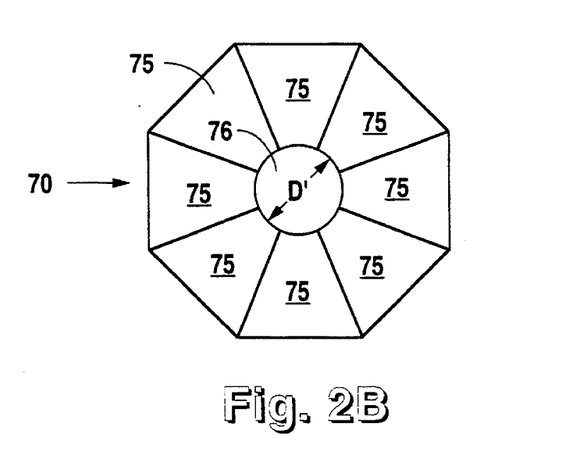
FIG. 2B schematically illustrates a top elevation of the prism.
Figure 2C:
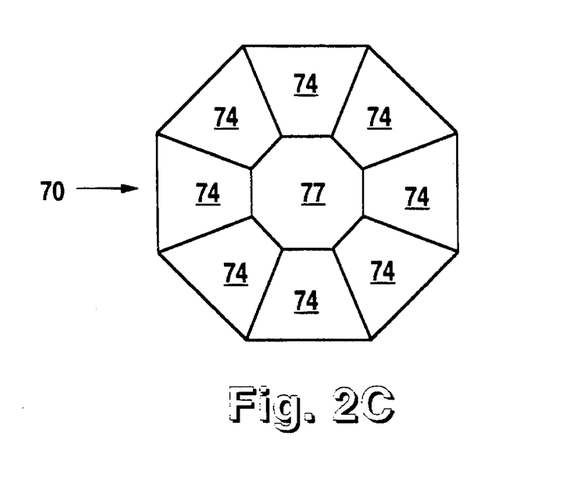
FIG. 2C schematically illustrates a bottom elevation of the prism.
Figure 3A:
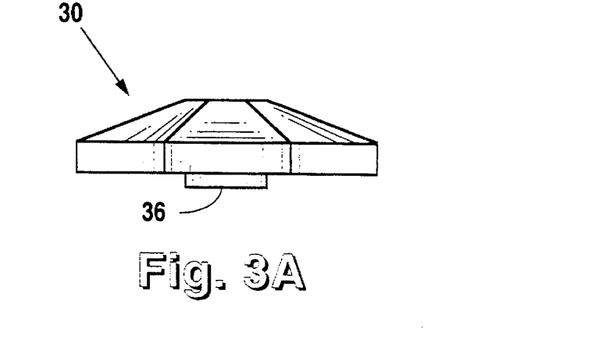
FIG. 3A schematically illustrates a side elevation of the reflector.
Figure 3B:
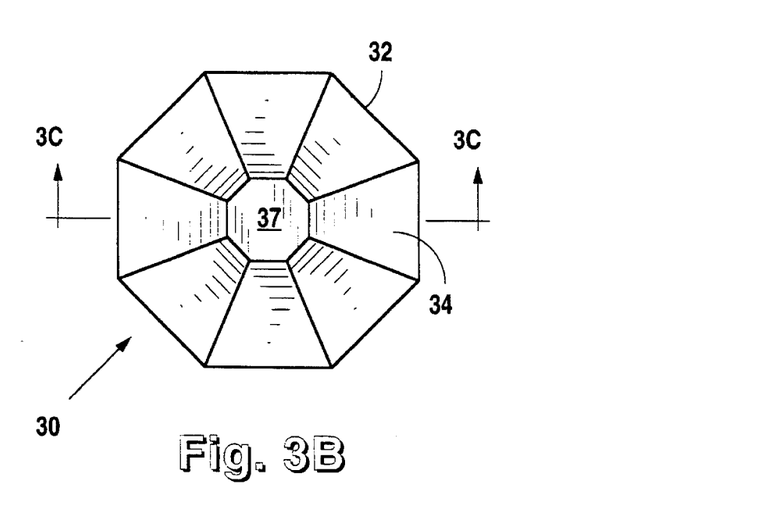
FIG. 3B schematically illustrates a top elevation of the reflector.
Figure 3C:
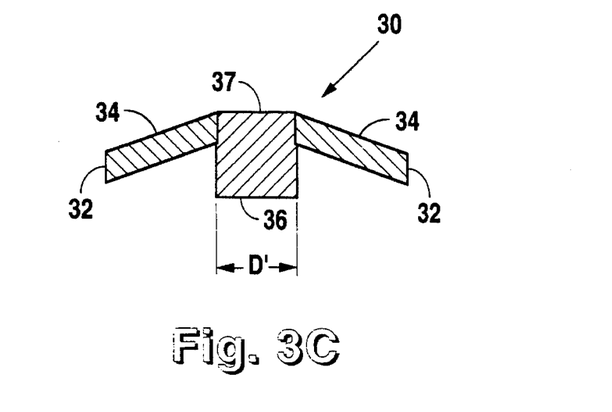
FIG. 3C schematically illustrates a cross-section of the reflector.

FIGS. 1-3 illustrate various views of and within a retroilluminating gonioprism 99 comprising a substantially frusto-pyramidal optical prism 70 having a longitudinal axis XX which is substantially collinear with the optical axis (not separately labeled) of optical prism 70. Optical prism 70 comprises a prism base 71, at least three substantially similarly shaped prism sides 73, and a substantially concave posterior surface 77 (preferably having a radius of curvature of about 9 mm to substantially match corneal curvature) opposite prism base 71. Each prism side 73 comprises a relatively larger substantially plane portion 74 oriented oblique to axis XX (preferably at an angle of about 20 to about 30 degrees) and a relatively smaller substantially plane portion 72 oriented substantially parallel to said axis XX. Plane portions 72 result because the at least one substantially convex surface 75 of prism base 71 must be spaced a predetermined amount from substantially plane portion 74 along axis XX to obtain the desired optical corrections as determined by ray tracing as described herein.

Prism base 71 is the optical prism anterior surface and said anterior surface comprises at least one substantially convex surface 75. At least a portion of light entering optical prism 70 through posterior surface 77 is at least partially reflected from at least one prism side portion 74 and exits prism 70 through at least one convex surface 75 substantially focussed external to prism 70. Note that convex surface(s) 75 are substantially spherical in preferred embodiments because of the ease of fabrication inherent in the specification of spherical curvature. However, both the optical resolution and field of view obtainable with retroilluminating gonioprism 99 can be improved for certain eye structures and/or areas in the anterior chamber through use of substantially cylindrical or substantially toroidal convex surface(s) 75 instead of substantially spherical surface(s) 75. In preferred embodiments of retroilluminating gonioprism 99, the convex surface(s) are configured to substantially optically correct astigmatism of oblique incidence and to substantially restore parallelism between a line-of-sight from an observer to the gonioprism and the axis XX. Ray tracings to determine desired optical corrections for astigmatism and parallelism are made using techniques well known to those of skill in the art and incorporated in a commercially available computer program entitled BEAM 4 OPTICAL RAY TRACER, copyright 1989 by Stellar Software, P.O. Box 10183, Berkeley, Calif. 94709.

A plurality of fiber optics 50,51 are coupled to the periphery of posterior surface 77 through their (preferably optically sealed) locations in perforations 49 within outer wall 48 of double-wall housing 45. Note that although only two fiber optics 50,51 are illustrated in FIG. 1A, preferred embodiments of retroilluminating gonioprism 99 may comprise more than two fiber optics arranged substantially symmetrically around posterior surface 77 to project light through perforations 49 beyond posterior surface 77 in a direction substantially parallel to the axis XX as schematically illustrated in FIG. 1A. Such light can then provide scleral scatter light beneath the gonioprism and retroillumination for anterior chamber structures.

In retroilluminating gonioprism 99, a reflector 30 is positioned proximate prism base 71 and coupled to optical prism 70 through center pin 36. Reflector 30 comprises at least one plano-flat lens 32 oriented obliquely (preferably at an angle of about 60 to about 80 degrees) with respect to axis XX to reflect at an angle oblique to axis XX at least a portion of light traveling substantially parallel to axis XX and striking reflector 30. The reflector 30 schematically illustrated in FIGS. 3A–3C comprises eight plano-flat lenses 32 substantially symmetrically arranged around center pin 36 and coupled to each other and to pin 36 because this reflector 30 embodiment is intended to be used with the embodiment of optical prism 70 which is schematically illustrated in FIGS. 2A–2C. The eight sides 73 of prism 70 are preferably rotationally aligned with the eight lenses 32 so that if a ray of light traveling within prism 70 in a plane containing axis XX is (preferably totally internally) reflected from substantially any part of portion 74 of a side 73, that ray will then pass through a single lens 32. Stated another way, each lens 32 is preferably aligned with prism base 71 in the manner schematically illustrated in FIG. 1A. Note that to reduce light reflections within the retroilluminating gonioprism, antireflective coatings (preferably one-quarter wavelength magnesium fluoride) may be applied to surfaces 34 of lenses 32 and/or to convex surfaces 75.

Note in the illustrated embodiment of the retroilluminating gonioprism 99, each preferred path of imaging light rays through the assembly comprising reflector 30 and prism 70 will be substantially centered in a lens 32 and a substantially convex anterior surface 75. Since no light rays are expected to travel substantially along axis XX or within the central portions of reflector 30 and prism 70 surrounding axis XX, top surface 37 of pin 36 is made opaque (and preferably non reflective) in FIG. 3C. Such an opaque surface may, in various embodiments of the retroilluminating gonioprism 99, be located anywhere along axis XX from surface 37 to depression 76 as long as it makes opaque at least a portion of reflector 30 and is substantially centered about axis XX. Opaque surface 37 (and analogous opaque surfaces) prevent accidental retinal burns when high-energy light beams are directed through prism 70. Without such an opaque surface, light beams directed into the retroilluminating gonioprism 99 could possibly travel through prism 70 in the direction of arrow L in FIG. 1A, passing out of posterior surface 77 without striking any part of portion 74 of a side 73. Thus, the beam could then proceed substantially undeviated to the retina where it could cause injury. Opaque surface 37, as described above and (one example of which is) schematically illustrated in FIG. 3C substantially precludes such accidental injury during use of the retroilluminating gonioprism of the present invention.

Note that the diameter D of pin 36 is intended to fit closely into depression 76 in prism base 71 to aid in maintaining the desired coupling between reflector 30 and prism 70. Depression 76 is preferably substantially centered among substantially convex anterior surfaces 75 on prism 70. The size of diameter D is preferably determined empirically and/or analytically to maximize visibility of eye structures through retroilluminating gonioprism 99.

To absorb and/or diffuse high-energy light traveling in the direction indicated by arrow L in FIG. 1A and being reflected from reflector 30, a light baffle 20 is positioned adjacent to reflector 30 and coupled to reflector 30 and optical prism 70 through internal flange 24 and inner wall 46, the assembly comprising reflector 30 and prism 70 effectively being clamped together between internal flange 24 and support surface 44 of inner wall 46 and support surface 43 of outer wall 48. Light baffle 20 is preferably glued, welded or press fit to outer wall 48 to assure structural integrity of retroilluminating gonioprism 99. In such an assembly, movement of prism 70 with respect to inner wall 46, outer wall 48 and light baffle 20 in a direction lateral to axis XX is substantially restrained by vertical restraint surfaces 42 of inner wall 46 which bear on plane portions 72 of prism 70. Light baffle 20 is configured to absorb at least a portion of light which, after traveling substantially parallel to axis XX (i.e., in the direction of the arrow L in FIG. 1A), strikes reflector 30 and is reflected obliquely with respect to axis XX from reflector 30 toward said light baffle 20. Light baffle 20 is schematically illustrated in FIG. 1A in a hollow and open-ended substantially right circular cylindrical form with a ridged internal surface 22. Such a surface will promote multiple reflection (of about 4 percent of incident light at each reflection) from various portions of internal surface 22 of light reflected from reflector 30 to internal surface 22 as described above. Additionally, when such light is substantially monochromatic, ridges of internal surface 22 may be spaced and of a predetermined depth to increase the likelihood of destructive interference among interacting reflected wavefronts. In another preferred embodiment, internal surface 22 may comprise lampblack or analogous material to approximate a blackbody surface which will preferably absorb at least about 70 percent of light incident on it.

A substantially conical double-wall housing 45 comprising an inner wall, to shield prism sides 73 from stray light, liquids and solid matter, and an outer wall, is coupled to prism 70 as described above. At least a portion of fiber optics 50,51 is substantially symmetrically arranged between inner wall 46 and outer wall 48 in frusto-conical space 47, with outer wall 48 comprising a plurality of fenestrations 49 as described above for allowing light from fiber optics 50,51 to be transmitted from double-wall housing 45. An elongated hollow handle 60 is firmly coupled (as by welding or gluing) to double-wall housing 45 and comprises at least a portion of fiber optics 50,51 within hollow handle 60 for coupling fiber optics 50,51 to an external light source (not shown) via an intermediate fiber optic (not shown) mechanically coupled to connector 62 (as by screw threads) and optically coupled to optical coupler 52 through light port 64.

What is claimed is:

1. A gonioprism, comprising
   a substantially frusto-pyramidal optical prism having a longitudinal axis and comprising a prism base, at least three substantially similarly shaped prism sides, and a substantially concave posterior surface opposite said prism base, said prism base being an anterior surface and said anterior surface comprising at least one substantially convex surface, wherein at least a portion of light entering said prism through said posterior surface is at least partially reflected from at least one prism side and exits said prism through said at least one substantially convex surface substantially focussed external to said prism;

a plurality of fiber optics coupled to said posterior surface to project light beyond said posterior surface;

a reflector proximate said prism base and coupled to said optical prism, said reflector comprising at least one plano-flat lens oriented obliquely with respect to said prism longitudinal axis to reflect at an angle oblique to said longitudinal axis at least a portion of light traveling substantially parallel to said longitudinal axis and striking said reflector;

a light baffle adjacent to said reflector and coupled to said reflector and said optical prism, said light baffle being configured to absorb at least a portion of light which, after traveling substantially parallel to said longitudinal axis, strikes said reflector and is reflected obliquely with respect to said longitudinal axis from said reflector toward said light baffle;

a substantially conical double-wall housing coupled to said prism, said double-wall housing comprising an inner wall to shield said prism sides and an outer wall, at least a portion of said fiber optics being substantially symmetrically arranged between said inner and outer walls and said outer wall comprising a plurality of fenestrations for allowing light from said fiber optics to be transmitted from said double-wall housing; and an elongated hollow handle firmly coupled to said double-wall housing and comprising at least a portion of said fiber optics within said hollow handle for coupling said fiber optics to an external light source.

2. The gonioprism of claim 1 wherein each said prism side comprises an air interface at which at least a portion of light entering said prism through said posterior surface would be totally internally reflected.

3. The gonioprism of claim 1 wherein each said prism side comprises a substantially reflective metallic film.

4. The gonioprism of claim 1 wherein said optical prism comprises a substantially transparent plastic.

5. The gonioprism of claim 1 wherein said reflector additionally comprises at least one antireflective coating.

6. The gonioprism of claim 1 wherein said optical prism anterior surface additionally comprises at least one antireflective coating.

7. The gonioprism of claim 1 wherein said light baffle comprises a hollow and open-ended substantially right circular cylindrical form having a longitudinal axis substantially collinear with said optical prism longitudinal axis and having a ridged internal surface to facilitate multiple reflection and absorption of light directed obliquely at said ridged internal surface.

8. The gonioprism of claim 1 wherein said light baffle comprises a hollow and open-ended substantially right circular cylindrical form having a longitudinal axis substantially collinear with said optical prism longitudinal axis and having an internal surface coated to approximate a blackbody to facilitate absorption of light directed at said internal surface.

9. The method of claim 8 wherein said plano-flat lens is positioned between about 60 degrees and about 80 degrees oblique to a line from the observer to the gonioprism anterior surface.

10. The method of claim 8 wherein said light baffle absorbs at least about 70 percent of light reflected to said light baffle from said plano-flat lens.

11. The gonioprism of claim 1 additionally comprising an opaque surface making at least a portion of said reflector opaque, said surface being substantially centered about said longitudinal axis.

12. The gonioprism of claim 11 wherein said opaque surface is substantially nonreflective.

13. The gonioprism of claim 1 wherein said gonioprism anterior surface is configured to substantially correct astigmatism of oblique incidence and to substantially restore parallelism between a line-of-sight from an observer to said gonioprism and said gonioprism longitudinal axis.

14. A gonioprism, comprising a substantially frusto-pyramidal optical prism having a longitudinal axis and comprising a prism base and eight substantially similarly shaped prism sides, all of said prism sides being oriented at substantially equal oblique angles with respect to said prism longitudinal axis, said prism further comprising a substantially spherically concave posterior surface opposite said prism base, and said prism base being an anterior surface, said anterior surface comprising a substantially regularly shaped depression substantially centered on said longitudinal axis, and said prism base further comprising a plurality of substantially spherically convex surfaces equal in number to said prism sides and spaced substantially evenly around and substantially contiguous with said centered depression, wherein at least a portion of light entering said prism through said posterior surface is at least partially reflected from at least one prism side and exits said prism through said at least one substantially convex surface substantially focussed external to said prism;

a plurality of fiber optics spaced substantially evenly around and coupled to said posterior prism surface to project light beyond said posterior surface substantially parallel to said longitudinal axis;

a reflector proximate said prism anterior surface and coupled thereto, said reflector comprising a plurality of substantially similarly shaped plano-flat lenses equal in number to said prism sides, said plano-flat lenses being spaced substantially evenly around and coupled to a center pin, said center pin being sized and shaped to fit closely within said anterior surface depression, all of said plano-flat lenses being oriented at substantially equal oblique angles with respect to said prism longitudinal axis to reflect at an angle oblique to said longitudinal axis at least a portion of light traveling substantially parallel to said longitudinal axis and striking said reflector;

a light baffle proximate said reflector and coupled to said reflector and said prism, said light baffle being configured to absorb light which, after traveling substantially parallel to said longitudinal axis, strikes said reflector and is reflected obliquely with respect to said longitudinal axis from said reflector toward said light baffle;

a substantially conical double-wall housing coupled to said prism, said housing comprising an inner wall to shield said prism sides and an outer wall, said fiber optics being substantially symmetrically arranged between said inner and outer walls and said outer wall comprising a plurality of fenestrations for allowing light from said fiber optics to be transmitted from said housing; and an elongated hollow handle firmly coupled to said double-wall housing and comprising at least a portion of said fiber optics within said hollow handle for coupling said fiber optics to an external light source.

15. The gonioprism of claim 14 wherein each said prism side comprises an air interface at which at least a portion of light entering said prism through said posterior surface would be totally internally reflected.

16. The gonioprism of claim 14 wherein each said prism side comprises a substantially reflective metallic film.

17. The gonioprism of claim 14 wherein said optical prism comprises a substantially transparent plastic.

18. The gonioprism of claim 14 wherein said reflector additionally comprises at least one antireflective coating.

19. The gonioprism of claim 14 wherein said optical prism anterior surface additionally comprises at least one antireflective coating.

20. The gonioprism of claim 14 wherein said light baffle comprises a hollow and open-ended substantially right circular cylindrical form having a longitudinal axis substantially collinear with said optical prism longitudinal axis and having a ridged internal surface to facilitate multiple reflection of light directed obliquely at said ridged internal surface.

21. The gonioprism of claim 14 wherein said light baffle comprises a hollow and open-ended substantially right circular cylindrical form having a longitudinal axis substantially collinear with said optical prism longitudinal axis and having an internal surface coated to approximate a blackbody to facilitate absorption of light directed at said internal surface.

22. The gonioprism of claim 14 wherein each said prism side is oriented at an angle of about 25 to about 30 degrees with respect to said optical prism longitudinal axis.

23. The gonioprism of claim 14 additionally comprising an opaque surface making at least a portion of said reflector opaque, said surface being substantially centered about said longitudinal axis.

24. A method of reducing reflection of light from a gonioprism anterior surface to an observer using the gonioprism to observe ocular structures, the gonioprism having an optical axis substantially collinear with its longitudinal axis, and the method comprising inserting a plano-flat lens between the observer and the gonioprism anterior surface;

positioning said plano-flat lens oblique to a line-of-sight from the observer to the gonioprism anterior surface;

providing a light baffle to absorb at least a portion of light reflected from said plano-flat lens, the light having traveled substantially along a line from the observer toward the gonioprism anterior surface; and configuring the gonioprism anterior surface to substantially correct astigmatism of oblique incidence and to substantially restore parallelism between said line-of-sight and the gonioprism optical axis.

* * * * *